(12) United States Patent
Blom et al.

(10) Patent No.: US 6,984,665 B2
(45) Date of Patent: Jan. 10, 2006

(54) METHODS FOR THE INHIBITION OF ATROPHY OR FOR TREATMENT OR PREVENTION OF ATROPHY-RELATED SYMPTOMS IN WOMEN

(75) Inventors: Taru Blom, Nousiainen (FI); Paula Grönroos, Turku (FI); Kaija Halonen, Rusko (FI); Pirkko Härkönen, Turku (FI)

(73) Assignee: Hormos Medical Corporation, Turku (FI)

( * ) Notice: Subject to any disclaimer, the term of this patent is extended or adjusted under 35 U.S.C. 154(b) by 354 days.

(21) Appl. No.: 10/162,708

(22) Filed: Jun. 6, 2002

(65) Prior Publication Data

US 2003/0036566 A1 Feb. 20, 2003

Related U.S. Application Data

(63) Continuation-in-part of application No. PCT/FI01/00414, filed on May 2, 2001.

(51) Int. Cl.
*A61K 31/19* (2006.01)

(52) U.S. Cl. .................................................... 514/721
(58) Field of Classification Search ................. 514/721
See application file for complete search history.

(56) References Cited

U.S. PATENT DOCUMENTS

| | | | |
|---|---|---|---|
| 5,352,699 A | 10/1994 | Jackson | |
| 5,747,059 A | 5/1998 | Korsgaard et al. | |
| 5,750,576 A | 5/1998 | DeGregorio et al. | |
| 5,912,273 A | 6/1999 | Degregorio et al. | |
| 6,037,379 A | 3/2000 | Härkönen et al. | |
| 6,245,819 B1 | 6/2001 | Halonen et al. | |
| 2001/0034340 A1 | 10/2001 | Pickar | |

FOREIGN PATENT DOCUMENTS

| | | |
|---|---|---|
| EP | 0 664 124 A1 | 7/1995 |
| EP | 1 125 582 A2 | 8/2001 |
| WO | WO 96/07402 A1 | 3/1996 |
| WO | WO 97/32574 A1 | 9/1997 |
| WO | WO 01/54699 A1 | 8/2001 |
| WO | WO 02/07718 A1 | 1/2002 |

OTHER PUBLICATIONS

K.C. Baynes et al., "Selective oestrogen receptor modulatros: a new paradigm for HRT," Curr Opin Obstet Gynecol 10(3):189-192, Jun. 1998.

M.W. DeGregorio et al., "Hormone replacement therapy and breast cancer: revisiting the issues," J Am Pharm Assoc 38(6):738-744, Nov.-Dec. 1998, (online abstract).

L. Kangas, "Biochemical and pharmacological effects of toremifene metabolites," Cancer Chemother Pharmacol 27: 8-12, 1990, XP 000675248.

M.M. Kennedy, "Tamoxifen and the endometrium: review of 102 cases and comparison with HRT-related-and non-HRT-related endometrial pathology," Int J Gynecol Pathol 18(2):130-137, Apr. 1999 (online abstract).

B.H. Mitlak et al., "Selective Estrogen Receptor Modulators," Drugs 57(5):653-663, May 1999.

Q. Qu et al., "Selective Estrogenic Effects of a Novel Tripheylethylene Compound, FC127la, on Bone, Cholesterol Level, and Reproductive Tissues in Intact and Ovariectomized Rats," Endocrinology 141(2):809-820, 2000 (online—20 pages).

M. Whitehead, "Treatment for menopausal and post-menopausal problems: present and future," Baillieres Clin Obstet Gynaecol 10(3):515-530, Sep. 1996 (online abstract).

*Primary Examiner*—Vickie Kim
(74) *Attorney, Agent, or Firm*—Rothwell Figg Ernst & Manbeck

(57) ABSTRACT

This invention relates to a method for inhibition of skin atrophy, or epithelial or mucosal atrophy in women, or to a method for treatment or prevention of symptoms related to said atrophy, said method comprising administering to the woman an effective amount of the compound of formula (I)

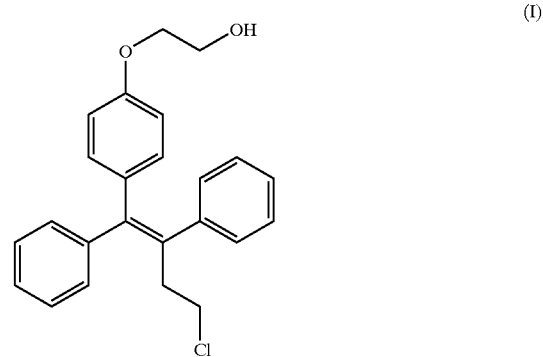

(I)

or a geometric isomer, a stereoisomer, a pharmaceutically acceptable salt, an ester thereof or a metabolite thereof.

3 Claims, 3 Drawing Sheets

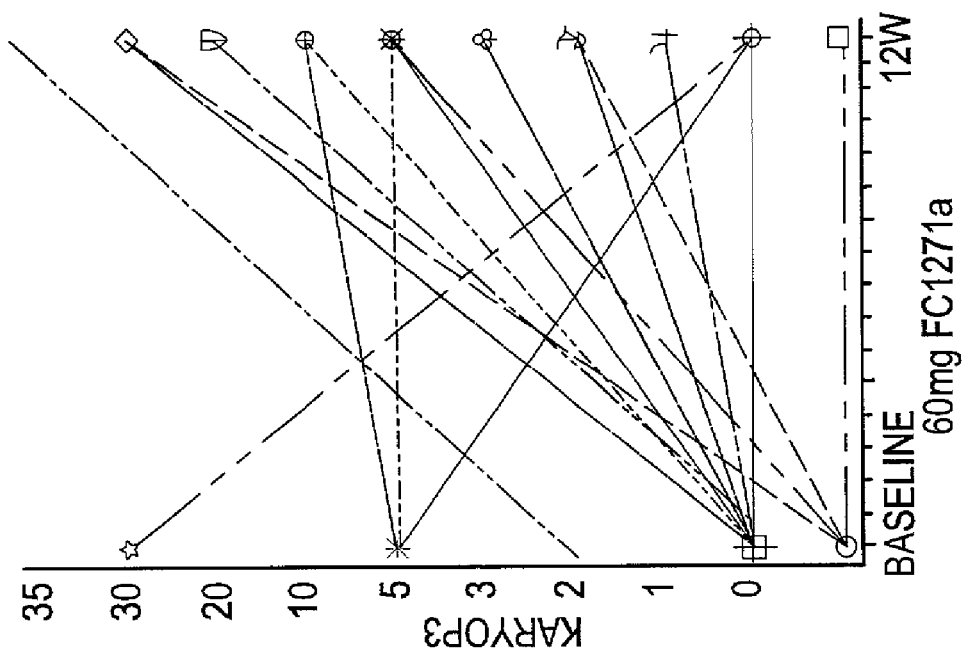
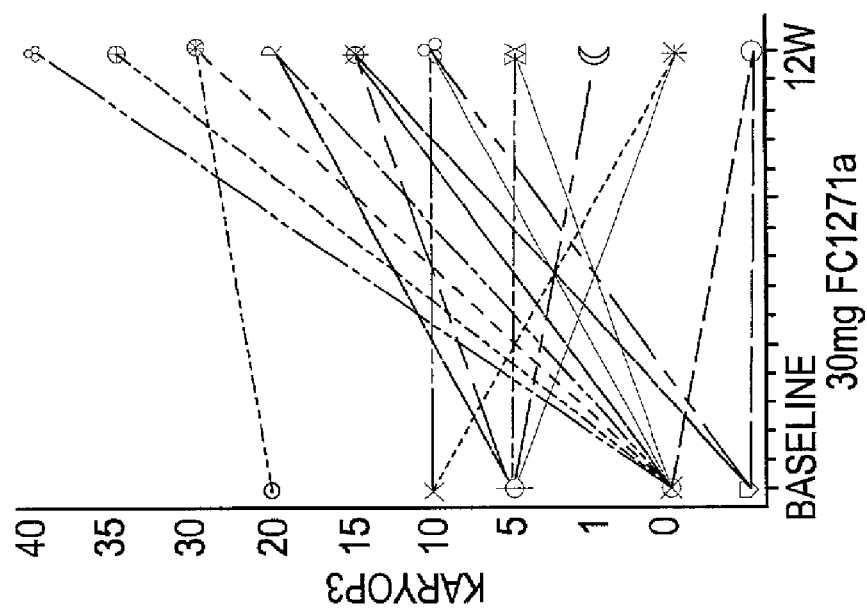

METHODS FOR THE INHIBITION OF ATROPHY OR FOR TREATMENT OR PREVENTION OF ATROPHY-RELATED SYMPTOMS IN WOMEN

CROSS-REFERENCE TO RELATED APPLICATIONS

The present application is a continuation-in-part of International Application No. PCT/FI01/00414 filed 2 May 2001 designating the U.S., which was published under PCT Article 21(2) in English as International Publication No. WO 02/07718, and which claims priority to U.S. patent application Ser. No. 09/625,199, filed 21 Jul. 2000, now U.S. Pat. No. 6,245,819, each application being incorporated by reference herein in its entirety.

FIELD OF THE INVENTION

This invention relates to a method for the inhibition of skin atrophy, epithelial or mucosal atrophy in women, especially women during or after the menopause. The invention also concerns prevention or treatment of atrophy-related symptoms in women, especially women during or after menopause.

BACKGROUND OF THE INVENTION

The publications and other materials used herein to illuminate the background of the invention, and in particular, cases to provide additional details respecting the practice, are incorporated by reference and listed in the Bibliography.

During and after menopause, elderly women commonly develop symptoms which are due to estrogen deficiency. These symptoms include hot flashes, sweating, insomnia, depression, vaginal dryness, urinary incontinence, nausea, pain, osteoporosis, coronary heart disease, breast tenderness, oedema, fatigue, decreased sexual activity, as well as subsequent psychosocial problems (Payer, 1990; Rekers, 1990). In addition, estrogens are suggested to have neuroprotective effects. Thus, declining estrogen concentrations may negatively affect the mental activities of aging women (Schneider & Finch, 1997; Wickelgren, 1997). Estradiol is known to be excellent in the treatment of climacteric symptoms, and its use in the treatment of these symptoms is rapidly increasing. However, estrogens cause an increased risk of endometrial and breast cancers. It is possible to decrease the carcinogenicity of endometrial cancer by sequential progestin administration, but the risk of breast cancer is not diminished by progestins. The carcinogenicity risk limits the length of estrogen replacement therapy, although it would be very useful to continue the therapy long term, due to the protective effects of estrogens in the bone, in the cardiovascular system, in the central nervous system, and for urinary symptoms.

"SERM"s (selective estrogen receptor modulators) have both estrogen-like and antiestrogenic properties (Kauffman & Bryant, 1995). The effects may be tissue-specific as in the case of tamoxifen and toremifene which have estrogen-like effects in the bone, partial estrogen-like effect in the uterus and liver, and pure antiestrogenic effect in breast cancer. Raloxifene and droloxifen are similar to tamoxifen and toremifene, except that their antiestrogenic properties dominate. Based on the published information, all SERMs are more likely to cause menopausal symptoms than to prevent them. They have, however, other important benefits in elderly women: they decrease total and LDL cholesterol, thus deminishing the risk of cardiovascular diseases, and they may prevent osteoporosis and inhibit breast cancer growth in post-menopausal women. There are also almost pure antiestrogens under development. They are mainly aimed at the treatment of breast cancer (Wakeling & Bowler, 1988).

The compound (deaminohydroxy)toremifene, which also is known under the code FC-1271a or the generic name ospemifene, has relatively weak estrogenic and antiestrogenic effects in the classical hormonal tests (Kangas, 1990). It has antiosteoporosis actions and it decreases total and LDL cholesterol levels in both experimental models and in human volunteers (International patent publications WO 96/07402 and WO 97/32574). It also has antitumor activity in an early stage of breast cancer development in an animal breast cancer model. Ospemifene is the first SERM which has been shown to have beneficial effects in climacteric syndromes in healthy women.

The European patent application EP 664124 A1 suggests the use of raloxifene or related compounds for the inhibition of skin atrophy or vaginal atrophy, especially in postmenopausal women.

SUMMARY OF THE INVENTION

According to one aspect, this invention concerns a method for inhibition of skin atrophy, or epithelial or mucosal atrophy in women, said method comprising administering to the woman an effective amount of the compound of formula (I)

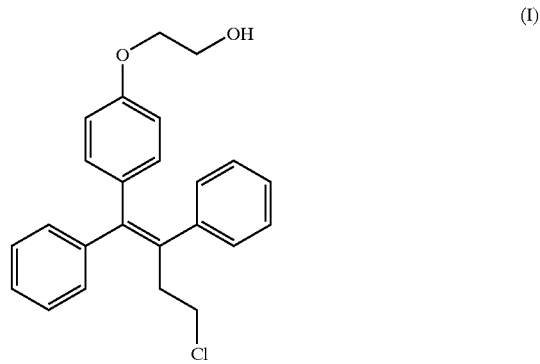

or a geometric isomer, a stereoisomer, a pharmaceutically acceptable salt, an ester thereof or a metabolite thereof.

According to another aspect, this invention concerns a method for treatment or prevention of symptoms related to skin atrophy, or to epithelial or mucosal atrophy in women, said method comprising administering to the woman an effective amount of the compound of formula (I)

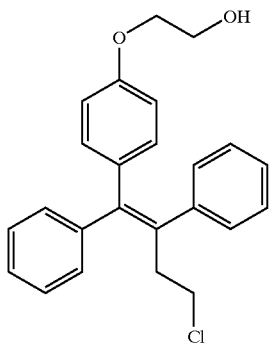

or a geometric isomer, a stereoisomer, a pharmaceutically acceptable salt, an ester thereof or a metabolite thereof.

BRIEF DESCRIPTION OF THE DRAWINGS

FIGS. 1A to 1D show changes (from start to 12 weeks' treatment) in the karyopyknosis index for superficial cells of the vaginal epitelium for the individuals treated daily with 30 mg ospemifene, i.e. FC-1271a (1A), 60 mg FC-1271a (1B), 90 mg FC-1271a (1C), and 60 mg raloxifene (1D).

DETAILED DESCRIPTION OF THE INVENTION

Figure 1D:
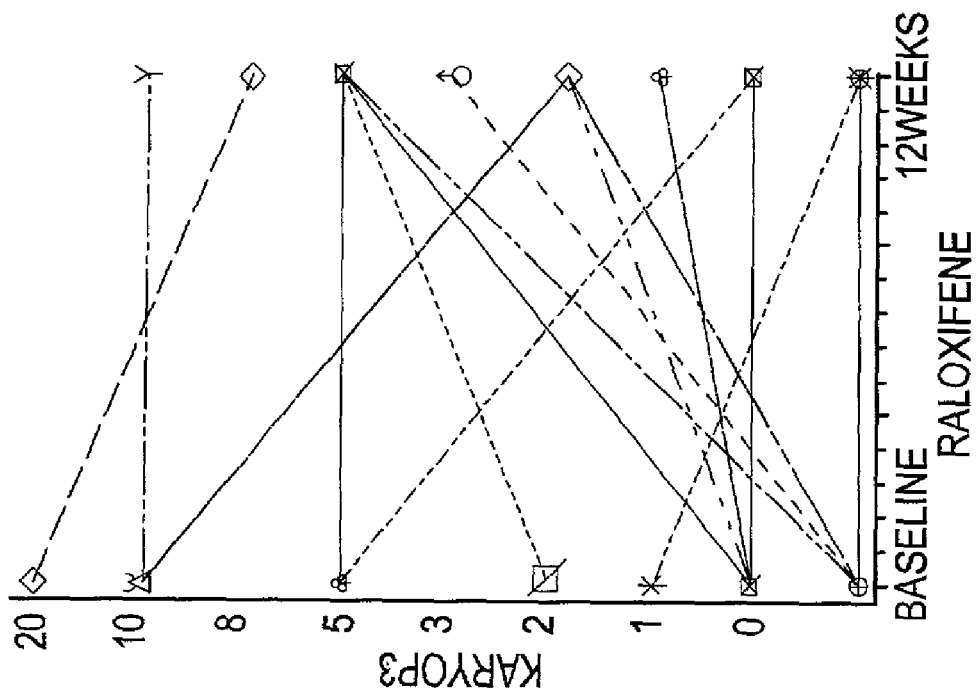
Figure 1C:
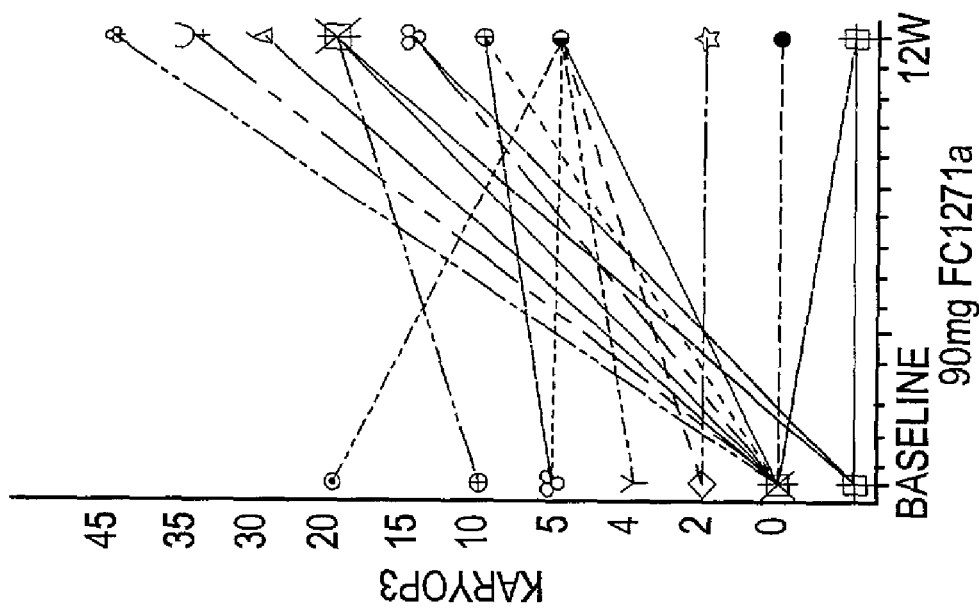

The methods according to this invention are particularly useful for women during or after the menopause. However, the methods according to this invention is not restricted to women in this age group.

This invention relates particularly to the use of the estrogen receptor modulator ospemifene in women during or after the menopause. Ospemifene is the Z-isomer of the compound of formula (I) and it is one of the main metabolites of toremifene, is known to be an estrogen agonist and antagonist (Kangas, 1990; International patent publications WO 96/07402 and WO 97/32574).

The term "metabolite" shall be understood to cover any (deaminohydroxy)toremifene metabolite already discovered or to be discovered. As examples of such metabolites can be mentioned the oxidation metabolites mentioned in Kangas (1990) on page 9 (TORE VI, TORE VII, TORE XVIII, TORE VIII, TORE XIII), especially TORE VI and TORE XVIII, and other metabolites of the compound.

The use of mixtures of isomers of compound (I) shall also be included in this invention.

A particular form of atrophy to be inhibited is urogenital atrophy. Symptoms related to urogenital atrophy can be divided in two subgroups: urinary symptoms and vaginal symptoms.

As examples of urinary symptoms can be mentioned micturation disorders, dysuria, hematuria, urinary frequency, sensation of urgency, urinary tract infections, urinary tract inflammation, nocturia, urinary incontinence, urge incontinence and involuntary urinary leakage.

As examples of vaginal symptoms can be mentioned irritation, itching, burning, maladorous discharge, infection, dyspareunia, leukorrhea, vulvar pruritus, feeling of pressure, postcoital bleeding, vaginal dryness and difficulty in sexual arousal.

The effect of atrophy of the skin is cosmetic, but can also be associated with pathological conditions such as decreased ability of the skin to undergo wound healing. Atrophy or aging of skin appears as change of smoothness and texture causing roughness in look and feel on the outer surface of the skin, change of elasticity of the skin effecting the mechanical properties of the skin, and changes in skin pigmentation. Skin aging in postmenopausal women can also be measured as decrease in the mitotic rate of keratinocytes, changes in dermal thickness and decrease in glucosaminoglucans and soluble collagen which are linked to the moisture content of the skin.

The new and surprising effect of ospemifene was found in a clinical study. In this study, raloxifene (60 mg/day) or ospemifene at different doses were given to elderly female volunteers for a period of 3 months. At the dose levels of 30, 60 and 90 mg of ospemifene daily, a significant decrease in vaginal atrophy was observed. An improved sexual activity was also reported. These properties are new and unique among the known selective estrogen receptor modulators (SERMs) and indicate that ospemifene at the doses from 25 mg to slightly lower than 100 mg daily, particularly 30 to 90 mg daily, can be successfully used to alleviate symptoms derived from atrophy, especially urogenital atrophy in women during or after the menopause. Furthermore, ospemifene has a superior profile of estrogenic and antiestrogenic effects when compared to any known antiestrogen or SERM compound.

Ospemifene has been found to alleviate many symptoms related to urogenital atrophy, both urinary symptoms and vaginal symptoms. Ospemifene has also been found to alleviate sexual dysfunction and to increase the sexual activity. Types and causes of female sexual dysfunction are particularly desire disorders, arousal disorders, orgasmic disorders and painful intercourse (dyspareunia). Most of these are due to hormonal reasons, especially to reduced estrogen and testosterone concentrations. Vaginal atrophy is one of the main causes of female sexual dysfunction and will typically develop after the menopause when the estrogen concentrations decrease. Typically this leads to painful intercourse, which indirectly may influence on any type of sexual dysfunction, including psychological causes. In elderly women vaginal atrophy is often the main reason for decreased sexual activity. (Spector and Carey, 1990).

Estrogens and testosterone are useful pharmaceutical treatments of vaginal dryness and it is not surprising that pure antiestrogens like raloxifene cause vaginal dryness. Subsequently, the patients are not satisfied with the treatment which causes painful intercourse and will stop the therapy.

The compound (I) can according to this invention be administered by various routes such as oral, topical, transdermal, intravaginal or subcutaneous routes, of which oral or transdermal administration routes are the most preferable.

Suitable preparation forms include for example tablets, capsules, granules, powders, suspensions, syrups and transdermal formulations, ointments, creams, or gels. Also subcutaneous implants may be useful for prolonged use. For vaginal local delivery vaginal creams, gels, vagitories, vaginal tablets, pessaries or vaginal rings are preferred.

Experiments

A clinical phase I–II study was carried out to study the effects of ospemifene on endometrial thickness, endometrial pathology, (biopsy taken by curettage as described by Vuopala et al, 1982) and cervical smear in healthy postmenopausal female volunteers in the age range 55 to 69 years. Tolerability and pharmacokinetics were also assessed. Raloxifene (60 mg daily) was used as reference. Ospemifene was given perorally at the doses of 30, 60 and 90 mg daily. There were 29 volunteers at each dose level, as well as in the raloxifene group. Ospemifene was administered in gelatine capsules containing either 30, 60 or 90 mg of ospemifene. The thickness of the endometrium was evaluated by ultrasonography using a Hitachi EUB-405 instrument. The vaginal epithelium was assessed by karyopyknosis index which is a well known assessment method among the skilled persons. In this method, the vaginal fraction of the cervical smears is estimated as the percentage of the number of cells from different layers: the parabasal cell layer; the intermediate cell layer; and the superficial cell layer. Estrogenicity is seen by a shift towards superficial cell fraction. In postmenopausal women this fraction usually is close to zero and estradiol treatment increases the fraction close to 100. Samples were taken before and after the treatment (at 3 months).

The vaginal dryness symptoms were also assessed by using a visual analogue scale where the volunteers themselves recorded their subjective estimates. The scale is based on a 100-mm line on paper. The left end represents no symptom and the right end the worst possible symptom. The change from pre-treatment to 3 months estimates was assessed and considered to be indicative of the treatment efficacy.

There were no differences in the demographic data between the treatment groups in any of the pre-treatment measurements.

Assessment of the Vaginal Estrogenic Effect of Ospemifene

Table 1 below shows the change in maturity index for parabasal cells (MI 1) and maturity index for superficial cells (MI 3), after 3 months' administration of varying doses of ospemifene or raloxifene.

TABLE 1

Change in maturity index for parabasal cells and maturity index for superficial cells

| Compound and dose | MI 1 mean | MI 1 Sd | MI 3 mean | MI 3 sd |
|---|---|---|---|---|
| Ospemifene, 30 mg, (n = 21) | −40 | 42 | +12.4 | 13.6 |
| Ospemifene, 60 mg, (n = 20) | −26 | 39 | +5.5 | 13.4 |
| Ospemifene, 90 mg, (n = 22) | −48 | 44 | +12.5 | 14.0 |
| Raloxifene, 60 mg, (n = 19) | −2 | 34 | −0.3 | 4.1 | parabasal cells (MI 1): index 100 no estrogenicity; index 0 full estrogen
superficial cells (MI 3): index 100 full estrogen; index 0 no estrogenicity In FIGS. 1A to 1D there are shown changes (from start to 12 weeks' treatment) in the karyopyknosis index for superficial cells of the vaginal epithelium for the individuals treated daily with 30 mg ospemifene (1A), 60 mg ospemifene (1B), 90 mg ospemifene (1C), and 60 mg raloxifene (1D). In the Figures, the code FC-1271a is used instead of the generic name ospemifene.

Cervical smear assessments indicate that no one in the raloxifene group (FIG. 1D) had a significant change from baseline to post-treatment in the karyopyknosis index for superficial cells. Most of the individuals in the ospemifene groups had slight increases in the index, but in rest of the subjects the estrogenic effect was very weak, if measurable at all. In all cases the increase was small (<40 except for one case which was 45 in the 90 mg group) when compared to estradiol which is known to increase the index virtually by 100. A weak but statistically significant estrogenic effect in the cervical smear was therefore documented. No pathological changes were seen in any sample.

Figure 2:
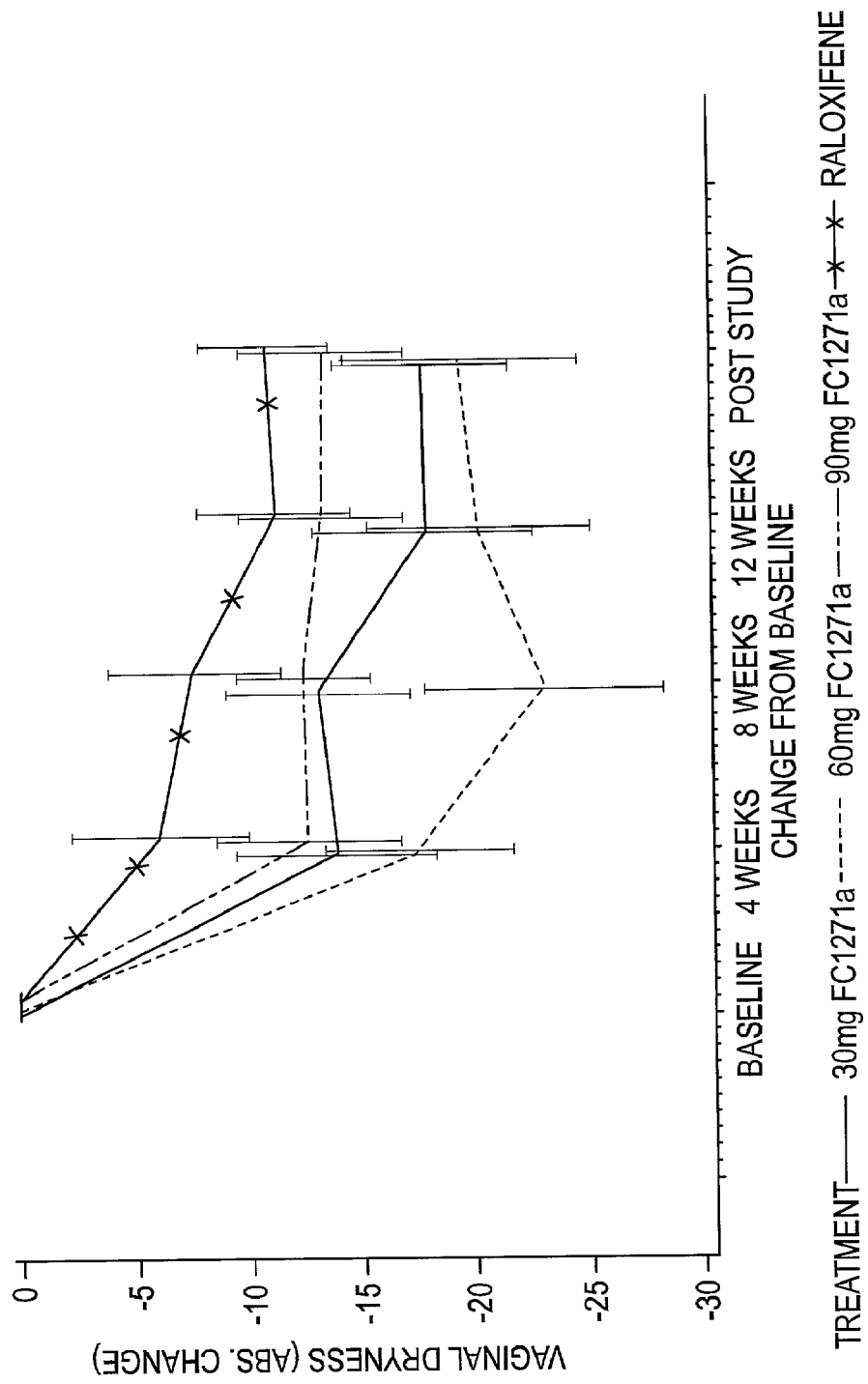
FIG. 2 shows the effect of 30 mg, 60 mg and 90 mg daily doses of FC-1271a and raloxifene (daily dose 60 mg) on vaginal dryness, assessed as the individuals' subjective estimates.

FIG. 2 shows that raloxifene caused only a minor decrease on vaginal dryness, assessed by the individuals' subjective estimate, while all the ospemifene dosage levels indicated a clear decreasing effect. The dose level 60 mg ospemifene daily gave the best result.

Assessment of the Endometrial Estrogenic Effect of Ospemifene

Ospemifene had a weak estrogenic effect on endometrial histology. This effect is clearly weaker than that seen with estrogen replacement therapy. There were no malignant findings in the endometrium. The thickness of the endometrium as assessed by ultrasonography showed only a minor, statistically not significant, increase in the thickness (average 0.2 mm, 0.5 mm and 0.5 mm) at the dose levels of 30, 60 and 90 mg, respectively. The measured values were always smaller than 8 mm, which is considered to be a thickness which is indicative for a physiologically significant estrogenicity of SERMs like tamoxifen (Hann et al, 1997; Lahti et al, 1993).

Effect on Urogenital Atrophy and Symptoms Related Thereto

In the clinical phase I and II studies, 241 posmenopausal women have been treated with ospemifene. 77 were treated with 25–30 mg, 78 with 50–60 mg, 78 with 90–100 and 8 with 200 mg daily dose of ospemifene. In the control groups, 47 were treated with placebo and 29 with raloxifene. Some of the subjects reported spontaneously alleviation of the symptoms associated with urogenital atrophy. The symptoms include both vaginal and urinary symptoms such as vaginal discomfort with irritation, itching, burning, smarting, dyspareunia, postcoital bleeding, vulvar itching and/or malodorous discharge and leukorrhea. The urinary symptoms alleviated in individual cases include urinary incontinence, recurrent urinary tract infections, micturition disorders, urinary frequency, nocturia, sensation of urgency, urge incontinence and involuntary urinary leakage. Also, the clinicians reported cases where signs of urogenital atrophy, such as vaginal pallor, petechiae, friability, vaginal dryness, vaginal mucosa atrophy and ulceration were alleviated by ospemifene.

Effect on Sexual Activity

In the clinical study, where the effects of ospemifene on quality of life and cardiovascular parameters were studied, the patients were asked for sexual activity. The questionnaire included "worsening" or "no effect" on sexual activity. Improvement on sexual activity was not asked. When 70 patients had been followed up for 6 weeks, 27 of them had spontaneously reported to the investigators increased sexual activity. Similar reports were independently obtained from different centers of the study. This strongly suggests that ospemifene has a positive effect on the sexual activity and quality of life.

The results indicate that ospemifene has a unique pharmacological profile with regard to estrogen-like effects on vaginal atrophy and insignificant endometrial effects. In these tissues the estrogenicity is markedly lower than that of the known SERMs tamoxifen and toremifene, but higher than that of raloxifene. In contrast to other SERMs, it does not cause menopausal symptoms. Actually ospemifene at the doses of 25 mg or more, and especially 30–90 mg daily, alleviated such symptoms. Ospemifene has an especially beneficial effect in that it decreases vaginal dryness and sexual dysfunction. Based on the present data, the optimal clinical dose is expected to be higher than 25 mg daily and lower than 100 mg daily. A particularly preferable daily dose is found in the range 30 to 90 mg. At the higher doses (100 and 200 mg daily), ospemifene shows properties more similar to those of tamoxifen and toremifene. Ospemifene is an especially valuable drug because it has an excellent tolerability. In addition, ospemifene decreases total and LDL cholesterol, increases HDL cholesterol, and prevents osteoporosis and early stage breast cancer. The present invention suggests that ospemifene and other compounds of formula (I) can be also used during menopause as hormone replacement therapy instead of estrogens, which are known to increase the risk of breast and endometrium cancers.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

BIBLIOGRAPHY

Delmas P D, Bjarnason N H, Mitlak B H, Ravoux A C, Shah A S, Huster W J, Draper M, Christiansen C: Effects of raloxifene on bone mineral density, serum cholesterol concentrations, and uterine endometrium in postmenopausal women. N Engl J Med 337: 1641–1647, 1997

Ettinger B, Genant H K, Cann C E: Long-term estrogen replacement therapy prevents bone loss and fractures. Ann Intern Med 102: 319–324, 1985

Hann L E, Giess C S, Bach A M, Tao Y, Baum H J, Barakat R R: Endometrial thickness in tamoxifen-treated patients: correlation with clinical and pathologic findings. Am J Roentgenol 168: 657–661, 1997

Gustafsson J -Å: Estrogen receptor β—getting in on the action? Nature Medicine 3: 493–494, 1997

Kangas L: Biochemical and pharmacological effects of toremifene metabolites. Cancer Chemother Pharmacol 27: 8–12, 1990

Kauffman R F, Bryant H U: Selective estrogen receptor modulators. Drug News Perspect 8: 531–539, 1995

Lahti E, Blanco G, Kauppila A, Apaja-Sarkkinen M, Taskinen P J, Laatikainen T: Endometrial changes in postmenopausal breast cancer patients receiving tamoxifen. Obstet Gynecol 81: 660–664, 1993

Palkowitz A D, Glasebrook A L, Thraser K J, Hauser K L, Short L L, Phillips D L, Muchi B S, Sato M, Shetler P K, Cullinan G J, Pell T R, Bryant H U: Discovery and synthesis of [6-hydroxy-3-[4-[2-(1-piperidinyl)ethoxy] phenoxy]-2-(4-hydroxyphenyl)]benzo[b]thiophene: a novel, highly potent, selective estrogen receptor modulator. Med Chem 40: 1407–1416, 1997

Payer L: The menopause in various cultures. In: A portrait of the menopause. Expert reports on medical and therapeutic strategies for the 1990s. Ed. Burger H & Boulet M, Parthenon Publishing, Park Ridge, N.J., USA, 1991. pp 3–22

Rekers H: Matering the menopause. In: A portrait of the menopause. Expert reports on medical and therapeutic strategies for the 1990s. Ed. Burger H & Boulet M, Parthenon Publishing, Park Ridge, N.J., USA, 1991. pp 23–43

Schneider L S, Finch C E: Can estrogens prevent neurodegeneration. Drugs & Aging 11: 87–95, 1997

Spector I P, Carey M P: Incidence and prevalence of sexual dysfunctions: a critical review of the empirical literature. Archives of Sexual Behaviour 19: 389–408, 1990.

Vuopala S, Kauppila A, Mikkonen M, Stenbäck F: Screening of asymptomatic postmenopausal women for gynecological malignancies, with special reference to endometrial sampling methods. Arch Gyncol 231: 119–127, 1982

Wakeling A E, Bowler J: Biology and mode of action of pure antiestrogens. J Steroid Biochem 30: 1–6, 1988

Wickelgren I: Estrogen stakes claim to cognition. Science 276: 675–678, 1997

What is claimed is:

1. A method for treatment or prevention of urinary symptoms related to urogenital atrophy in women, said method comprising administering to a woman an effective amount of the compound of formula (I)

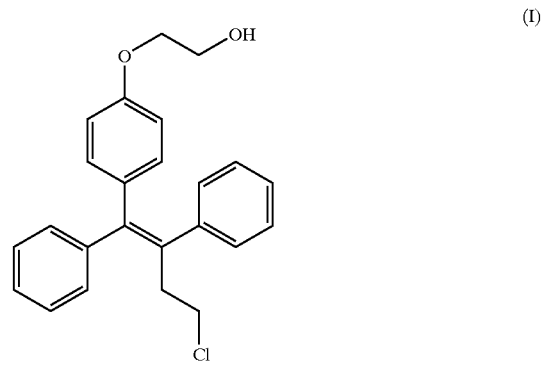

or a geometric isomer, a stereoisomer, a pharmaceutically acceptable salt, an ester thereof or a metabolite thereof wherein the urinary symptoms are micturation disorders, dysuria, hematuria, urinary frequency, sensation of urgency, urinary tract infections, urinary tract inflammation, nocturia or involuntary urinary leakage.

2. The method according to claim 1 wherein compound (I) is ospemifene.

3. The method according to claim 1 wherein compound (I), its isomer, salt or ester is administered orally, topically, transdermally, intravaginally or subcutaneously.

* * * * *

UNITED STATES PATENT AND TRADEMARK OFFICE
CERTIFICATE OF CORRECTION

PATENT NO. : 6,984,665 B2  
APPLICATION NO. : 10/162708  
DATED : January 10, 2006  
INVENTOR(S) : Taru Blom et al.

Page 1 of 1

It is certified that error appears in the above-identified patent and that said Letters Patent is hereby corrected as shown below:

COLUMN 3

Line 25, "epitelium" should read --epithelium--; and  
Line 38, "is" should read --are--.

COLUMN 4

Line 9, "effecting" should read --affecting--.

COLUMN 6

Line 31, "posmenopausal" should read --postmenopausal--.

COLUMN 8

Line 47, "thereof" should read --thereof,--;  
Line 48, "urinary" should read --said urinary--; and  
Line 51, "leakage." should read --leakage; and the said metabolite is selected from the group consisting of TORE VI, TORE VII, TORE XVIII, TORE VIII, and TORE XIII.--.

Signed and Sealed this

Twenty-sixth Day of June, 2007

JON W. DUDAS  
*Director of the United States Patent and Trademark Office*

UNITED STATES PATENT AND TRADEMARK OFFICE
CERTIFICATE OF CORRECTION

| | | |
|---|---|---|
| PATENT NO. | : 6,984,665 B2 | Page 1 of 1 |
| APPLICATION NO. | : 10/162708 | |
| DATED | : January 10, 2006 | |
| INVENTOR(S) | : Taru Blom et al. | |

It is certified that error appears in the above-identified patent and that said Letters Patent is hereby corrected as shown below:

On the Title Page

Under "Related U.S. Application Data" (field (63)), immediately after "Continuation-in-part of application No. PCT/FI01/00414, filed on May 2, 2001" add ", which is a continuation of application serial no. 09/625,199, now Pat. No. 6,245,819."

In the Specification

In column 1, line 14, immediately after "02/07718, and which" delete "claims priority to" and insert in its place "is a continuation of".

Signed and Sealed this

Fifteenth Day of March, 2011

David J. Kappos
*Director of the United States Patent and Trademark Office*